Figure 1:
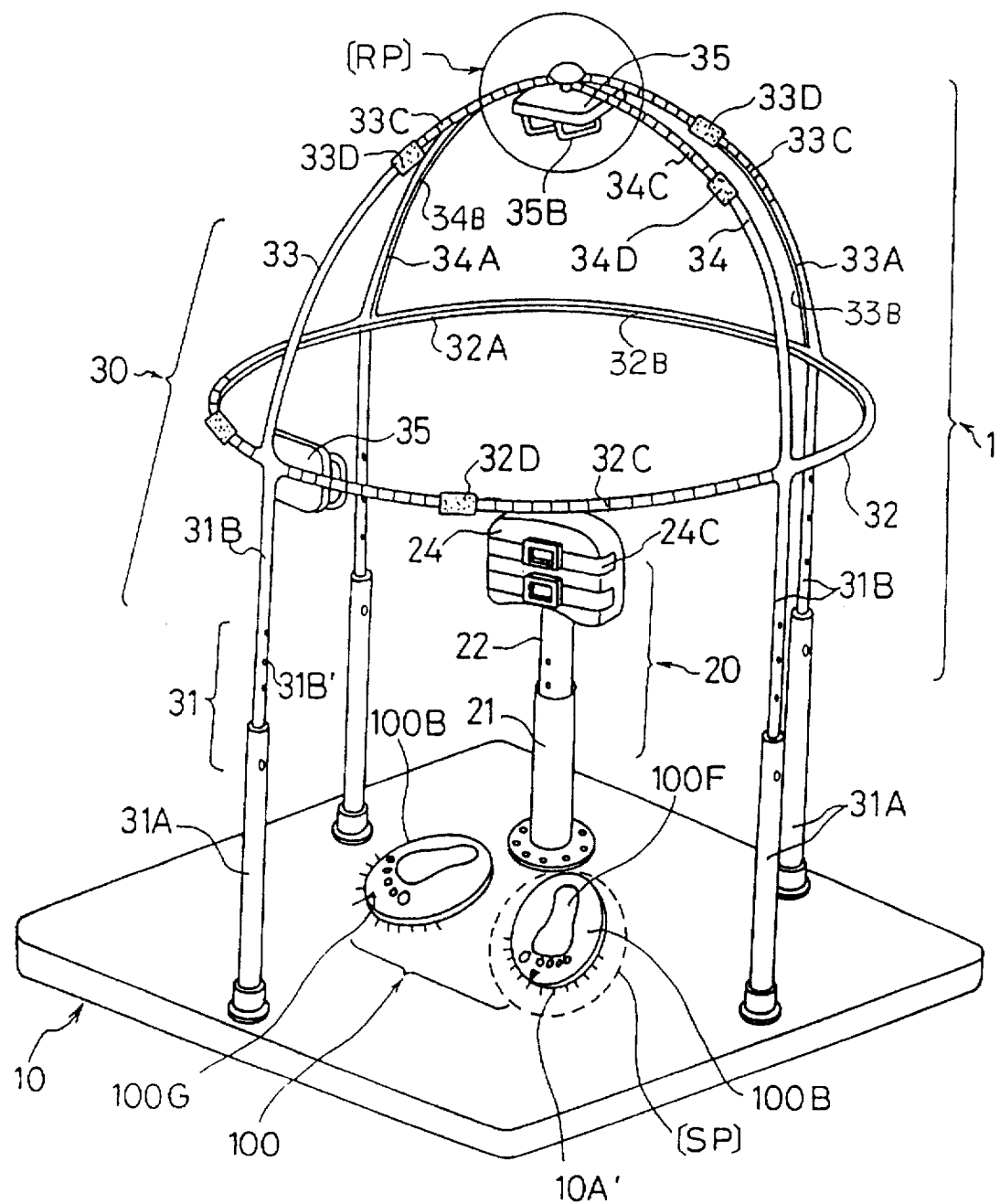

United States Patent [19]

Soejima

[11] Patent Number: 5,785,665
[45] Date of Patent: Jul. 28, 1998

[54] BODY AXES MEASURING DEVICE AND METHOD FOR CONTROLLING DEVIATION OF BODY AXIS

[76] Inventor: Noboru Soejima, 1-11-305, Takanawa 1-chome, Minato-ku, Tokyo 108, Japan

[21] Appl. No.: 564,245
[22] PCT Filed: Apr. 28, 1994
[86] PCT No.: PCT/JP94/00726
§ 371 Date: Dec. 20, 1995
§ 102(e) Date: Dec. 20, 1995
[87] PCT Pub. No.: WO95/29631
PCT Pub. Date: Nov. 9, 1995
[51] Int. Cl.$^6$ .................... A61B 5/103; A61B 5/11
[52] U.S. Cl. ......................... 600/594; 600/595
[58] Field of Search .................... 128/781, 774; 600/782, 594, 595

[56] References Cited

U.S. PATENT DOCUMENTS

| | | | |
|---|---|---|---|
| 2,324,672 | 7/1943 | Bierman | 128/781 |
| 4,033,329 | 7/1977 | Gregory | 128/781 |
| 4,425,713 | 1/1984 | Rotella | 128/774 X |
| 4,492,236 | 1/1985 | Pile | 128/781 |
| 5,094,249 | 3/1992 | Marras | 128/781 |
| 5,443,079 | 8/1995 | Greenawalt | 120/781 |
| 5,474,086 | 12/1995 | McCormick | 128/782 |

FOREIGN PATENT DOCUMENTS

| | | | |
|---|---|---|---|
| 0144528 | 6/1985 | European Pat. Off. | 128/781 |
| 50-4887 | 1/1975 | Japan . | |
| 55-2999 | 1/1980 | Japan . | |
| 63-318928 | 12/1988 | Japan . | |
| 1109128 | 8/1984 | U.S.S.R. | 128/781 |

Primary Examiner—Richard J. Apley
Assistant Examiner—William LaMarca
Attorney, Agent, or Firm—Varndell Legal Group

[57] ABSTRACT

Object of the present invention is to provide a device for capably measuring deviation of body axes around three axes as centers of backward-forward flection, leaning and twisting, and a method for correcting such body axis deviation. A measuring device comprises a means (20) for regionally fixing a user's body and a means (30) for detecting and measuring flection limits around a rolling axis, an pitching axis or an yawing axis while regionally fixing said user's body as a fulcrum, and a method for correcting a body axis which comprises detecting flection limits around a user's joint to regard a bisected point of thus detected limits as a body axis deviation and remanding or correcting said body axis deviation around one of a rolling axis, an pitching axis or an yawing axis by repeatedly twisting a body around the other two axes as fulcrums.

8 Claims, 5 Drawing Sheets

BODY AXES MEASURING DEVICE AND METHOD FOR CONTROLLING DEVIATION OF BODY AXIS

TECHNICAL FIELD

This invention relates to a device for capably measuring an actual angular deviation of a body axis and a method for controlling same around three body axes as centers of forward-backward bending and twisting movements of the body.

TECHNICAL BACKGROUND

Japanese Utility Model Publication No. 55-2,999, for example, describes a kind of athletic tool which has been conventionally known.

Such an athletic tool comprises a whirl-driven horizontal disc and a repeatedly fluctuating arc arm, the horizontal disc and the arm being actuated by a pair of motors to train the upper half of a trainee's body using changes in a relative position thereof under a condition in which the trainee on the disc grasps rings suspended from the arm.

With regard to a human body, it is well known that skeletal structures are joined by many joints which allow bending push-up and twisting movements. These movements comprise right-left leaning, forward-backward bending and right-left twisting of the body. It is also known that balance of mind and body as well as good health can be kept when these bending and twisting angles centering around the joints under a natural standing up condition are frontally symmetry and axes thereof are balanced each other.

Further, with regard to the control of unbalanced body axes, when body bending or twisting limits to both directions centering around a rolling axis (R), an pitching axis (P) and an yawing axis (Y) relating to the right-left leaning, forward-backward bending and the right-left twisting movements, respectively, show unbalanced measurements, it has been clinically confirmed that such an unbalance of either one of these axes (R), (P) or (Y) can be corrected by the forward-backward bending or twisting movements centering around the other two axes.

The above mentioned Utility Model only provides an athletic tool for training the upper half of a trainee's body. On the other hand, although the unbalance relating to the longitudinal, pitching and yawing axes, (R), (P) and (Y) as well as correction thereof are known in principle, any actual structure, tool or hardware for embodying this principle has not yet provided. As a matter of fact, it has been eagerly needed to develop a body axes measuring hardware and a method for controlling a body axis deviation.

Accordingly, it is an object of this invention to provide a device for measuring the body axes and a method for correcting the body axis deviation enough to meet such eager need.

DISCLOSURE OF THE INVENTION

The manner in which the above mentioned object of the present invention will be apparent from the following description. The most characteristic features of the present invention are:

1. A body axes measuring device comprising a means for regionally fixing a user's body and a means for detecting and measuring flection limits around a longitudinal, an pitching axis or an yawing axis while regionally fixing said user's body as a fulcrum;

2. A body axes measuring device as set forth in item 1, above, further comprising a means for fixing a user's waist and a means for recording changes in posture to both directions around at least one of a longitudinal, an pitching axis or an yawing axis of the use's waist;

3. A body axes measuring device as set forth in item 2, above, further comprising a horizontal circular flame, a backward-forward arc flame and a right-left arc flame with slides slidable on said flames for guiding an upper half of a user's body when the user changes posture thereof while keeping arm stretched, each of said flames having angular graduations and marking sleeves thereon;

4. A body axes measuring device as set forth in item 2 or 3, above, in which a guiding means for changing posture of an upper half of a user's body and a waist seat for fixing the user's waist are height-adjustable;

5. A body axes measuring device as set forth in item 1, above, further comprising foot discs for guiding angular changes of twisted legs to inner and outer directions around a user's groin joint and means for recording twist limits of said discs; and 6. A method for correcting a body axis which comprises detecting flection limits around a user's joint to regard a bisected point of thus detected limits as a body axis deviation and remanding or correcting said body axis deviation around one of a longitudinal, an pitching axis or an yawing axis by repeatedly twisting a body around the other two axes as fulcrums.

BRIEF DESCRIPTION OF THE INVENTION

Figure 2:
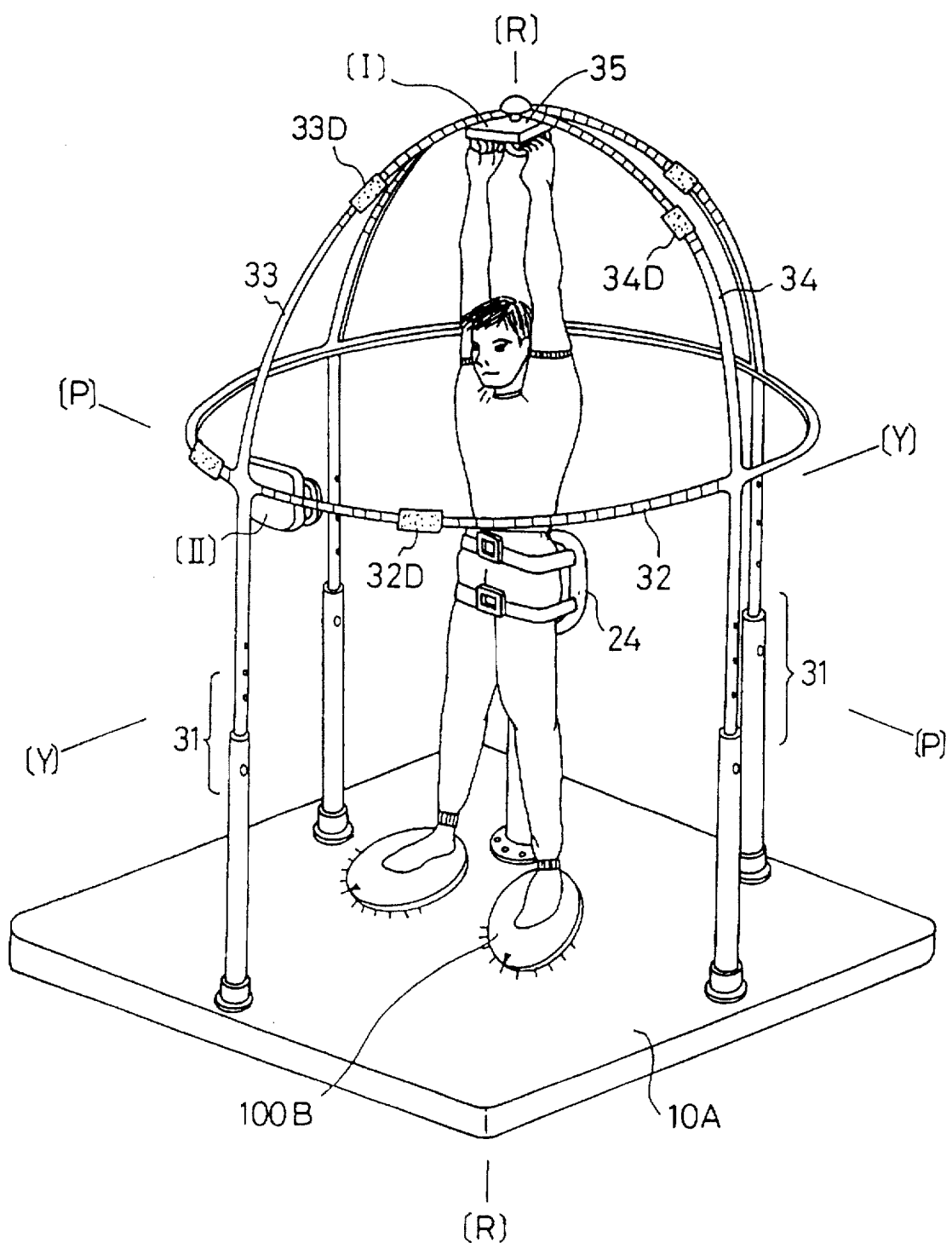
Figure 3:
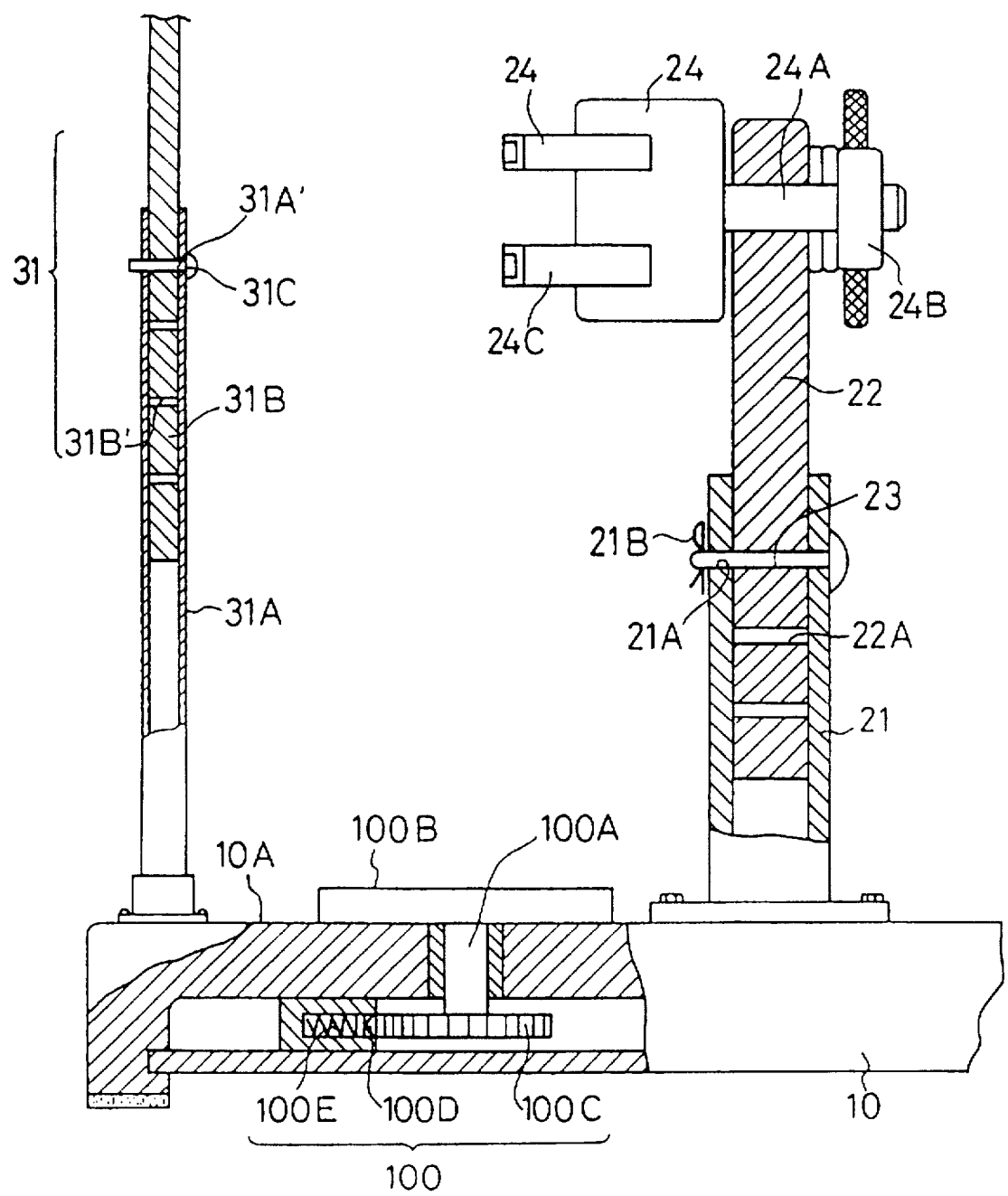
Figure 4:
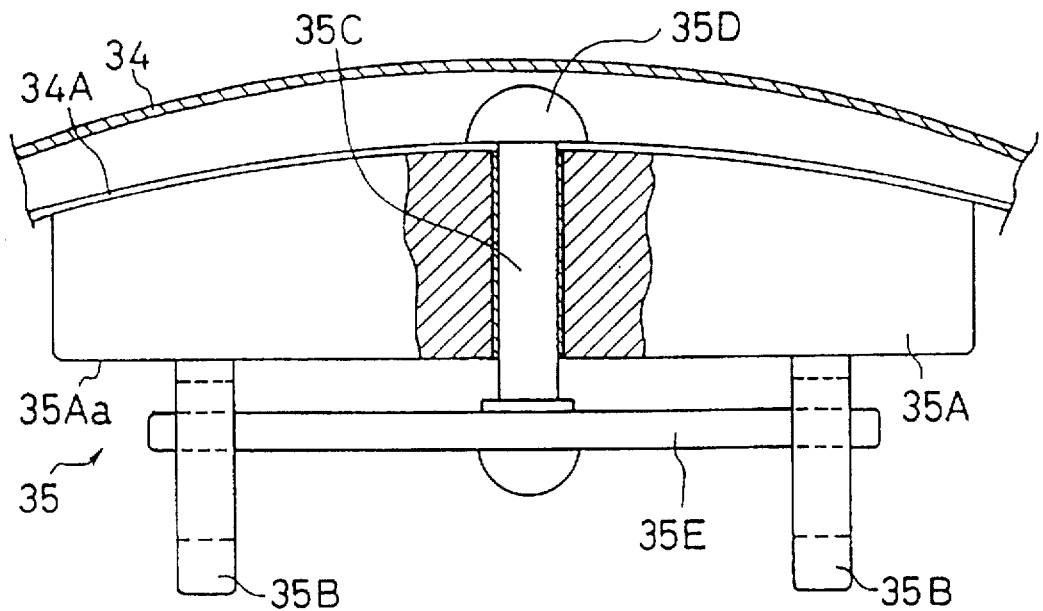
Figure 5:
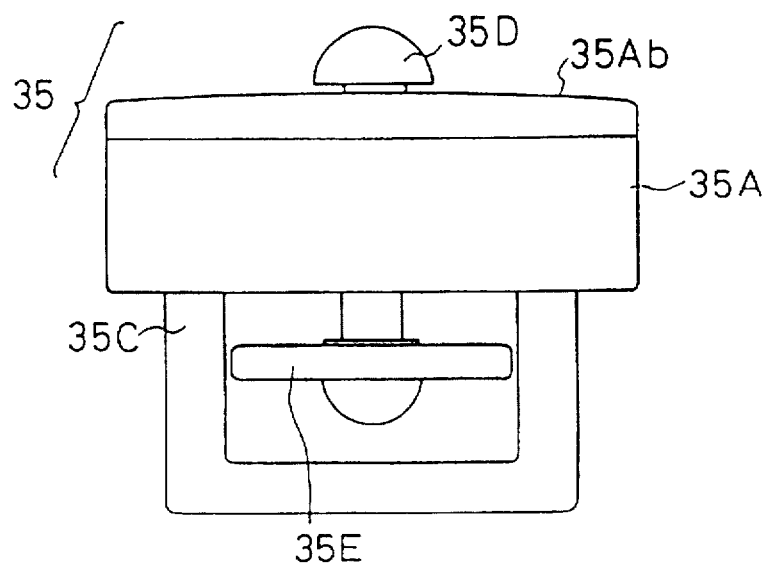
Figure 6:
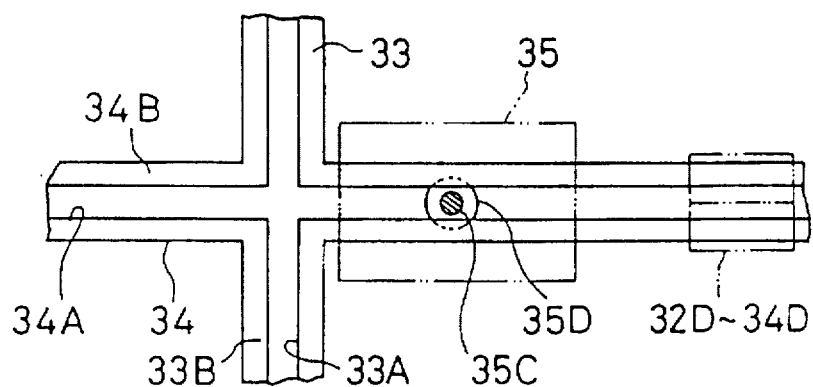
Figure 7:
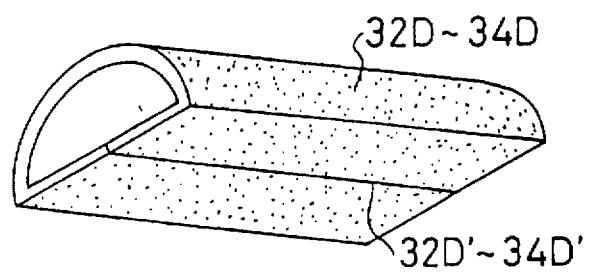
Figure 8:
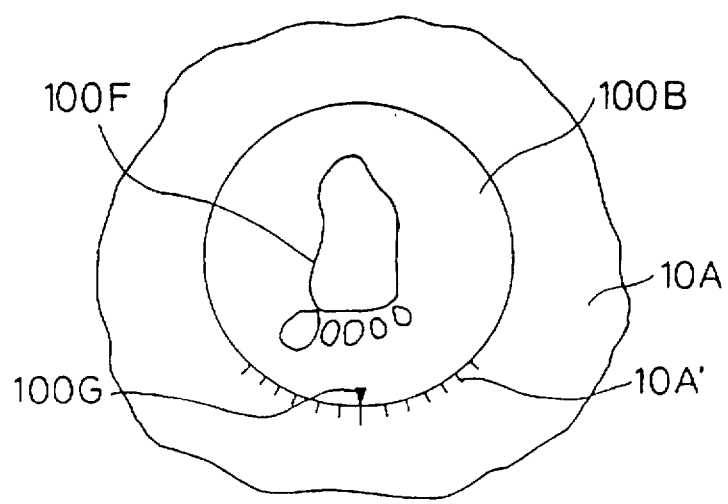

FIG. 1 is a perspective view illustrating an embodiment of the present device; FIG. 2 is a practical illustration of FIG. 1 used by a user; FIG. 3 is fragmentary sectional side view of FIG. 1; FIG. 4 is a front view in section of a slide shown in FIG. 1; FIG. 5 is a side view of a slide; FIG. 6 is a bottom view of a part (RP) circled by a solid line in FIG. 1.; FIG. 7 is a perspective view of marking sleeve; and FIG. 8 is a plan view of a part (SP) circled by a broken line in FIG. 1.

THE FORM TO CARRY OUT THE INVENTION

The present invention will now be described in detail by embodiments in connection with the accompanying drawings.

As perspectively shown in FIG. 1, a body axes measuring device (1) according to an embodiment of the present invention comprises a height-adjustable waist fixing means (20) mounted on a base plate means (10) and a height-adjustable measuring means (30) of a hemispherical basket shape, while the base plate means (10) is provided with a groin joint axis measuring means (100).

Each of these means (10), (20), (30) and (100) will be individually described in detail in the following.

(1) Waist Fixing Means (20)

As shown in FIG. 3, a vertical lever (22) is height-adjustablly inserted in a cylindrical post (21) vertically mounted on the base plate means (10) and is perforated to form a plurality of holes (22A). An adjusting pin (23) is then inserted through perforations (21A) of the cylindrical post (21) and one of the holes (22A) to securely set the vertical lever (22) to the cylindrical post (21). In FIG. 3, reference numeral (21B) designates a safety catch.

Further, a waist seat (24) covered with leather-cloth or other soft material is fixed to the vertical lever (22) in the vicinity thereof by means of a supporting shaft (24A) and a clamp (24B). The waist seat (24) is provided with a pair of waist belts (24C) for fixing a user's waist to the seat.

(2) Measuring Means (30)

As shown in FIGS. 1, 3, 4 and 5, a measuring means (30) is connected to the top of four adjustable supports (31) vertically mounted on the base plate means (10) so as to surround the waist fixing means (20). A backward-forward arc flame (33) and a right-left arc flame (34) cross at nearly right angle at top portions thereof and extend downward to a horizontal circular frame (32). The former frames (33) and (34) are connected to the latter frame (32) to form a basket-like structure. As sectionally shown in FIGS. 4 and 6, each frame (32), (33) and (34) is a hollow rail having a nearly semicircular cross section, which slidably holds therein a guide body (35D) of a slide (35) as will be described below, and has guide slits (32A), (33A) and (34A) along inside frame portions (32B), (33B) and (34B) for keeping a lever core (35C).

With respect to the adjustable supports (31) for supporting the horizontal circular flame (32), the backward-forward arc flame (33) and the right-left arc flame (34), as shown in FIGS. 1 and 3, four cylindrical supports (31A) are vertically mounted on the base plate means (10), while up-and-down levers (31B) are connected to the horizontal circular frame (32) at top portions and inserted into the supporting cylinders (31A) at bottom portions thereof. An adjusting pin (31C) is selectively inserted into perforations (31A') of the cylindrical supports (31A) as well as one of a plurality of holes (31B') perforated through the up-and-down lever (31B) so as to effectively make use of each frame (32), (33) and (34) depending on the user's height.

The horizontal circular frame (32) has angular graduations (32C) up to about 90° on upper and lower surface thereof from the front center of the user to right and left directions. On the other hand, each of the arc flames (33) and (34) also has backward-forward and right-left angular graduations (33C) and (34C), respectively, up to about 45° from their top center to respective directions. As shown in FIGS. 6 and 7, slide-and stop type marking sleeves (32D), (33D) and (34D) made of rubber or other material are detachably fitted to each of the flames (32), (33) and (34) through slit portions (32D'), (33D') and (34D').

With respect to the slide (35) slidably fitted on the horizontal circular flame (32) and the arc flames (33) and (34), a pair of protruding grips (35B) is mounted on an inner surface (35A*a*) of a main body (35A) thereof, which outer surface (34A*b*) being curved convexly. There are provided a hemispherical slider (35D) at an outer end of an axial lever (35C) slidablly pierced through the main body (35A) to slide it in each frame (32), (33) or (34), and a stopping lever (35E) at an inner end thereof. Both ends of the stopping lever (35E) are alocated in space between each grip (35B) and the main body (35) so that the user can grasp the grips (35B) and the stopping lever (35E) together, if necessary. When the stopping lever (35E) is thus grasped, the outer surface (35A*b*) of the main body (35A) is pressed to the inside flame portions (32B), (33B) and (34B), each frame (32), (33) or (34) is tightly bound between the slider (35D) and the outer surface (35A*b*), thereby allowing the slider (35) to stop arbitrarily on the flames.

(3) Groin Joint Axis Measuring Means (100)

As shown in FIGS. 1, 2 and 3, a foot disc (100B) is fixed on an upper end of a pivot (100A) pivotted to a base plate (10A) of the base plate means (100). A gear wheel (100C) is fixed to the pivot (100A) under the base plate (10A), rotation of which being halted by a stopper ball (100D) as a positioning device when the stopper ball (100D) is pressed toward the gear wheel (100C) by means of a pressing spring (100E). The foot disc (100B) has a footprint (100F) for putting on a user's foot correctly and a pointer (100G) for recording rotation angles thereon, while the base plate has rotational angular graduations (10A') to be pointed by the pointer (100G).

A manner to use the present embodiment will be described below.

(1) Body Axis Measurement Based on Movements of the Upper Half of the Body

When a user moves the upper half of the body, deviation of body axes is measured as in the following depending on the user's height, sitting height and leg length.

First of all, adjusting pins (31C) of four adjustable supports (31) mounted on the device (1) are pulled out thereof to vertically slide the level of up-and-down levers (31B) and cylindrical supports (31A). The adjusting pins (31C) are then inserted into holes (31B') and perforations (31A') to adjust height of the measuring means (30) to the base plate (10). On the other hand, the other adjusting pin (23) of the cylindrical post (21) is pulled out thereof to vertically slide the vertical lever inserted therein and is then put it in the perforations (21A) of the cylindrical post (21) and the hole (22A) of the vertical lever (22) to adjust height of the waist seat (24). The safety catch (21B) should be used to prevent the adjusting pin (23) from falling off. Finally, the user is allowed to stand on the base plate (11A) of the base plate means(20) while facing front and keeping the waist in contact with the waist seat (24). The user stretches arm thereof to grasp a pair of grips (35B) of the slide (35) after the waist is fixed to the waist seat (24) by means of a pair of waist belts (24C). The device (1) is now ready to measure angles of the body axis deviation.

As a matter of convenience, measurement of the deviation around the yawing axis (Y) will be described in the following.

The user leans the arm forward while keeping the posture shown in FIG. 2 and the waist fixing, thereby the slide (35) being slid forward from the upper position (I) to the lower one (II) on the backward-forward frame (33) over an arcing orbit.

Then, when the user twists the body to the right and left directions, the slide (35) moves to the same directions over an arcing orbit on the horizontal circular frame (32).

In such an instance, the axial lever (35C) of the slide (35) strikes a pair of making sleeves (32D) on the horizontal circular frame (32) and pushes them aside. Depending on an angular extent achieved by the user's up-and-down movement, the distance between the got away marking sleeves (32D) changes.

Accordingly, extent of movement of each making sleeve (32D) are shown by up-and-down angular graduations (32C) on the horizontal circular frame (32).

Flection limits of the user toward the yawing axis (Y) and right-left deviation thereof can be detected by visually observing the graduations.

When a similar measurement is conducted without using the present device (1), it is difficult to accurately detect such flection limits toward the yawing axis (Y) and the deviation thereto, because the user's waist and shoulder tend to move freely.

In the present embodiment, however, the user's waist is fixed to the waist seat (24) to always face the front and the arm is connected to the grips (35B) of the slide (35) without bending thereof, thereby keeping the arm straight and the shoulder static without any bending and swinging. This results in accuracy in detecting the flection limits toward the yawing axis (Y). Further, an angular center of the flection limits can be detected from positions where a pair of making sleeves (32D) stay, which apparently shows the deviation of body axis toward the yawing axis (Y).

For example, if a result of the above mentioned measurement is that up-and-down angles to the right and left directions facing to the front are 40° and 45°, respectively, the flection limit is 95°, i.e., the deviation of body axis is about 2.5° to the left direction.

A method for correcting the deviation of body axis thus detected will be described in the following.

This is a typical example of practically applied clinical correcting methods. The user swings up the arm with the slide (35) and returns to the first posture shown in FIG. 2, followed by further forward flection of the upper half of the body together with the slide (35) on the backward-forward arc frame (33), and again returns to the first posture. Then, the upper half of the body leans to the right direction while moving the slide (35) on the right-left frame (34) and returns to the posture shown in FIG. 2, again. That is, the upper half of the body is flexed forward around the pitching axis (P) and leaned to the right direction around the rolling axis (R).

It is desirable to reasonably repeat such a corrective training a few times as light athletics. The body axes are completely balanced through a series of movements, which results in outstanding corrective effects of the deviation of body axis.

It is clinically observed that the deviation to the right or left direction is clearly rehabilitated, the up-and-down angle of the upper half of the body is equal toward the right and left directions and the flection limits are considerably increased, when the same measurement toward the yawing axis (Y) is conducted.

As to the deviation of the body axis around the rolling axis (R) and the pitching axis (P), the measurement is similarly done. The upper half of the body is leaned to the right or left direction with the slide (35) while keeping the arm stretched to move the slide (35) on the right-left arc frame (34). The extent of movement is detected by the making sleeve (34D) on the backward-forward graduations to measure the flection limits and the deviation around the rolling axis. Similarly, the upper half of the body is leaned backward and forward to move the slide (35) on the backward-forward arc frame (33). The flection limits and the deviation around the pitching axis (P) are detected by the positions of the marking sleeves (33D) on the right-left graduations (33C). Correction of the deviation is done in a similar manner as described in the case of the yawing axis. The upper half of the body is twisted or leaned around the other two axes. The most effective measurement of the deviation of body axis and correction thereof can be conducted because of frontal fixation of the user's waist in both cases.

While muscular force of users of the present device (1) ranges widely due to difference in ages, sex, physical strength and the like, it would sometimes difficult for certain user to return by him- or herself to the posture shown in FIG. 2 from a condition in which the upper half of the body flexed or leaned backward-forward or to the right-left directions. In such a case, according to the present embodiment, the user can firmly grasp the grips (35B) together with the stopping lever (35E) so that the slide (35) is pressed to the backward-forward arc frame (33) or the right-left arc-frame (34) to stop thereof. Thus, the present device (1) is used easily and safely without danger.

(2) Body Axis Measurement Based on Movements of Lower Half of the Body

In order to measure the deviation of body axis around a groin joint, the user leaves go grips of the slide (35) while fixing the waist to the waist seat (24) similarly as described above, allows the arm to hang down naturally and places both feet within the footprint (100F) on the foot disc (100B) while standing up thereon straight.

In this situation, when the user twists both legs inside and outside, twist limits of the pointer (100G) painted on the foot disc (100B) are indicated by pointed angular graduations (10A') on the base plate (10A). The up-and-down angles of both legs to inner and outer directions are thus visually observed, which allows to measure the twist limits and the deviation.

Similarly as the above mentioned case in which the axial deviation is measured relating to the upper half of the body, for example, if the up-and-down angles of the right leg to the right and left directions are about 40° and 45°, respectively, it is considered that the body axis deviates 2.5° to the right direction. Correcting movements of such deviation is that the user rise the right foot from the foot disc (100B), moves it backward, returns it to the first position, opens it to the right direction and returns it to the first position. It is clinically confirmed that when a series of movements as described above are repeated a few times, the axial deviation of the groin joint is completely corrected and the body axes are balanced.

To slide the waist fixing means vertically, an electric or a hydrodynamic means may be used other than what is described in the present embodiment. Further, a variety of means including screws, rack and pinions, etc. may be used as a vertical slide means for the measuring means. It is to be understood that all of these means may be used as variations without departing the spirit and the scope.

INDUSTRIAL APPLICABILITY

As has been detailed above, the flection limits around three body axes, i.e., the rolling axis, the pitching and the yawing axes as well as the axial deviation can be accurately measured through the user's movements such as flection or twisting of the upper half of the body. Similarly, the flection limits and the axial deviation can be measured by detecting the twisting angle of both legs.

Because of the adjusting means employed to meet the user's body build, the present device can be used effectively and widely without restriction of ages, sex and the like.

In addition, the slide is provided with the stopping means to insure safety.

The deviation of body axis can be corrected only by reasonablly flexing or twisting the body around the axes without pain, thereby recovering the physical balance and considerably improving health and kinetic ability.

I claim:

1. A body axes measuring device comprising a frame, a body fixing means for regionally fixing a user's body and a measuring means for detecting and measuring flexion limits around a horizontal axis and along an arc above the user's body while regionally fixing the user's body as a fulcrum, said frame including adjustable supports attached to a base and having a bottom portion extending horizontally and a top portion forming an arc structure, and a circular frame extending horizontally and arranged between said top and bottom portions of said adjustable supports, whereby the arc structure facilitates the measuring along the arc above the user's body.

2. The body axes measuring device claimed in claim 1, wherein said measuring means includes a first slide movably attached to said arc and a second side movably attached to said circular frame.

3. The body axes measuring device claimed in claim 2, wherein said measuring means includes recording means for recording measurements of flection limits along said circular frame and along said arc.

4. The body axes measuring device claimed in claim 1, wherein said fixing means includes means for fixing a user's waist.

5. The body axes measuring device claimed in claim 1, wherein said adjustable supports are adapted to adjust to a height of the user's body, so that a user can grasp said first slide with fully extended arms.

6. The body axes measuring device claimed in claim 1, wherein said circular frame and said arch have angular graduations and marking sleeves thereon.

7. The body axes measuring device claimed in claim 5, wherein said fixing means includes a height adjustable waist seat for fixing a user's waist.

8. A body axes measuring device claimed in claim 1, further comprising foot discs for guiding angular changes of twisted legs to inner and outer directions around a user's groin joint and means for recording twist limits of said discs.

* * * * *